(12) United States Patent
Bhatt et al.

(10) Patent No.: US 9,776,985 B2
(45) Date of Patent: Oct. 3, 2017

(54) PROCESS FOR PREPARATION OF ALOGLIPTIN

(71) Applicant: Glenmark Pharmaceuticals Limited, Mumbai (IN)

(72) Inventors: Navin Ganesh Bhatt, Navi Mumbai (IN); Samir Naik, Thane (IN); Ajay Kumar Sharma, Pardesh (IN); Mahendra Joma Choraghe, Navi Mumbai (IN); Shekhar Bhaskar Bhirud, Mumbai (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 14/893,620

(22) PCT Filed: May 20, 2014

(86) PCT No.: PCT/IB2014/061554
§ 371 (c)(1),
(2) Date: Nov. 24, 2015

(87) PCT Pub. No.: WO2014/188334
PCT Pub. Date: Nov. 27, 2014

(65) Prior Publication Data
US 2016/0340333 A1   Nov. 24, 2016

(30) Foreign Application Priority Data
May 24, 2013  (IN) .......................... 1844/MUM/2013

(51) Int. Cl.
*C07D 401/04*  (2006.01)
*C07D 401/14*  (2006.01)

(52) U.S. Cl.
CPC ......... *C07D 401/04* (2013.01); *C07D 401/14* (2013.01)

(58) Field of Classification Search
CPC .......................... C07D 401/04; C07D 401/14
USPC .......................................... 544/309; 514/274
See application file for complete search history.

(56) References Cited

U.S. PATENT DOCUMENTS

| 8,222,411 B2 | 7/2012 | Feng et al. |
| 8,841,447 B2 | 9/2014 | Marom et al. |
| 2007/0066635 A1 | 3/2007 | Andres et al. |
| 2011/0306764 A1 | 12/2011 | Ludescher et al. |
| 2012/0029000 A1* | 2/2012 | Marom ................ A61K 31/513 514/274 |

FOREIGN PATENT DOCUMENTS

| CN | 1926128 A | 3/2007 |
| CN | 102942556 A | 2/2013 |
| CN | 103030631 A * | 4/2013 |
| WO | 2013046229 A1 | 4/2013 |

OTHER PUBLICATIONS

Machine-generated Translation of CN 103030631 (2013).*
Christopher et al., Pharmacokinetics, Pharmacodynamics, and Tolerability of Single Increasing Doses of thte Dipeptidyl Peptidase-4 Inhibitor Alogliptin in Healthy Male Subjects, Clinical Therapeutics, vol. 30, No. 3, pp. 513-527 (2008).*
J. Feng et al., "Discovery of Alogliptin: A Potent, Selective, Bioavailabie, and Efficacious Inhibitor of Dipeptidyl Peptidase IV," Journal of Medicinal Chemistry, 2007, pp. 2297-2300, vol. 50, No. 10.
L. Zhao-Wen, "Synthesis of Alogliptin Benzoate," Strait Pharmaceutical Journal, Sep. 2, 2011, pp. 214-215, (English Abstract Only).

* cited by examiner

*Primary Examiner* — Deepak Rao
(74) *Attorney, Agent, or Firm* — Ryan, Mason & Lewis, LLP

(57) ABSTRACT

Provided is a novel process for the preparation of alogliptin.

11 Claims, No Drawings

PROCESS FOR PREPARATION OF ALOGLIPTIN

PRIORITY

This application claims priority under 35 U.S.C. §371 to International Application No. PCT/IB/2014/061554, filed May 20, 2014 which claims the benefit of Indian Provisional Application No. 1844/MUM/2013, filed May 24, 2013, the contents of which are incorporated by reference herein.

FIELD OF INVENTION

The present invention relates to a novel process for preparation of alogliptin.

BACKGROUND OF THE INVENTION

Alogliptin which is chemically known as 2-({6-[(3R)-3-aminopiperidin-1-yl]-3-methyl-2,4-dioxo-3,4-dihydropyrimidin-1(2H)-yl}methyl)benzonitrile is represented structurally by a compound of formula I,

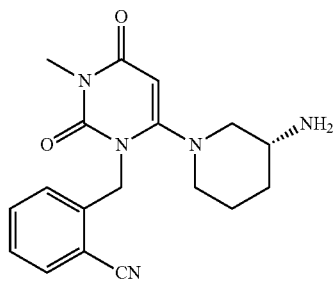

I

NESINA® tablets contain the active ingredient alogliptin, which is a selective, orally bioavailable inhibitor of the enzymatic activity of dipeptidyl peptidase-4 (DPP-4). Chemically, alogliptin is prepared as a benzoate salt, which is identified as 2-({6-[(3R)-3-aminopiperidin-1-yl]-3-methyl-2,4-dioxo-3,4-dihydropyrimidin-1(2H)-yl}methyl)benzonitrile monobenzoate.

NESINA is a dipeptidyl peptidase-4 (DPP-4) inhibitor indicated as an adjunct to diet and exercise to improve glycemic control in adults with type 2 diabetes mellitus.

The object of the present invention is to provide a novel process for the preparation of alogliptin via novel intermediate compounds.

SUMMARY OF THE INVENTION

The present invention provides a process for the preparation of alogliptin, a compound of formula I, or a salt thereof comprising:

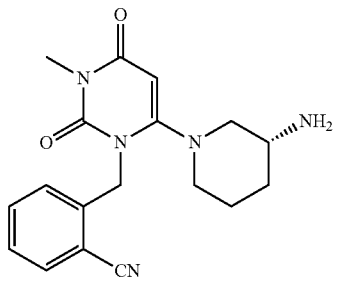

I a) methylating a compound of formula IV, to obtain a compound of formula V

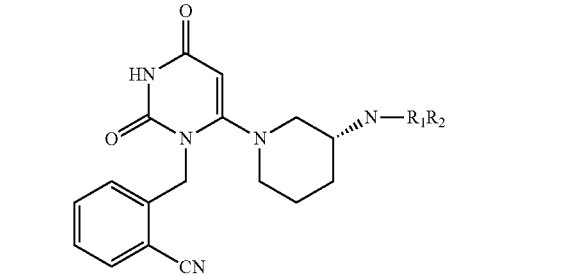

IV

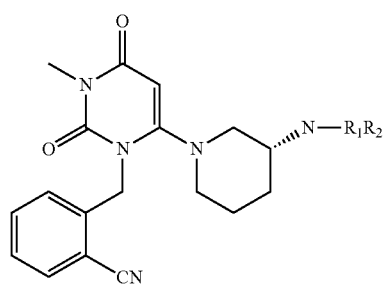

V wherein $R_1$ and $R_2$ together with the nitrogen to which they are attached form a phthalimido group, wherein the aromatic ring of the phthalimido group is unsubstituted or substituted with one or more $R_3$ substituents selected from the group consisting of halogen, alkyl, nitro and amino; or $R_1$ is H and $R_2$ is an amino protecting group selected from the group consisting of aralkyl, acyl, lower alkoxy-carbonyl, aralkyloxy-carbonyl, lower alkane sulfonyl, aryl sulfonyl, tri-(lower alkyl) silyl, 2-trialkylsilylethoxycarbamates, triphosgene, diphenylphosphine and sulfonylethoxycarbonyl; and b) deprotecting the compound of formula V to obtain compound of formula I.

The present invention provides a compound of formula IV

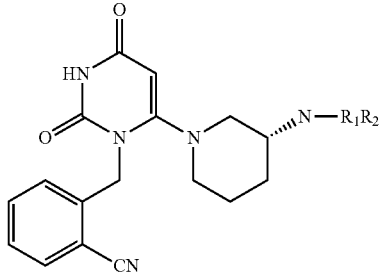

IV wherein $R_1$ and $R_2$ are as defined above.

The present invention provides the use of compound of formula IV or V in the preparation of alogliptin, a compound of formula I or a salt thereof.

DETAILED DESCRIPTION OF THE INVENTION

In one embodiment, the present invention provides a process for the preparation of alogliptin, a compound of formula I, or a salt thereof comprising:

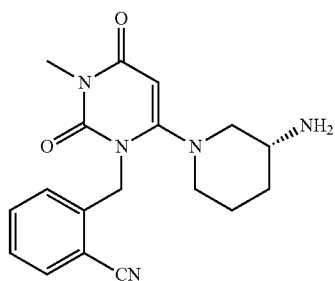

I a) methylating a compound of formula IV, to obtain a compound of formula V

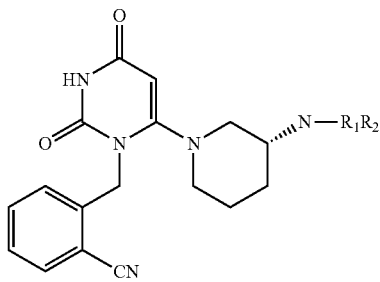

IV

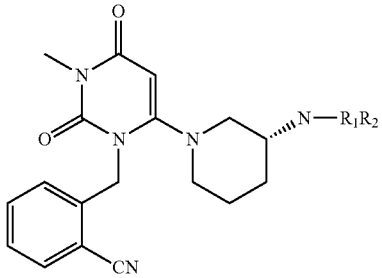

V wherein $R_1$ and $R_2$ together with the nitrogen to which they are attached form a phthalimido group, wherein the aromatic ring of the phthalimido group is unsubstituted or substituted with one or more $R_3$ substituents selected from the group consisting of halogen, alkyl, nitro and amino; or $R_1$ is H and $R_2$ is an amino protecting group selected from the group consisting of aralkyl, acyl, lower alkoxy-carbonyl, aralkyloxy-carbonyl, lower alkane sulfonyl, aryl sulfonyl, tri-(lower alkyl) silyl, 2-trialkylsilylethoxycarbamates, triphosgene, diphenylphosphine and sulfonylethoxy-carbonyl; and b) deprotecting the compound of formula V to obtain compound of formula I.

The term "halogen" as used herein means chloride, bromide, iodide. The term "alkyl" as used herein includes a straight or branched chain hydrocarbon containing from 1 to 6 carbon atoms. Representative examples of alkyl include, but are not limited to methyl, ethyl, n-propyl, isopropyl, n-butyl, sec-butyl, tert-butyl, n-pentyl, isopentyl, neopentyl, n-hexyl.

The term "aralkyl" as used herein includes benzyl, methoxybenzyl, 2,4-dimethoxybenzyl, p-nitrobenzyl, benzhydryl, trityl.

The term "acyl" as used herein includes formyl, acetyl, trihaloacetyl, propionyl, methoxyacetyl, methoxypropionyl, benzoyl, thienylacetyl, thiazolylacetyl, tetrazolylacetyl, thiazolylglyoxyloyl, thienylglyoxyloyl.

The term "lower alkoxy-carbonyl" as used herein includes methoxycarbonyl, ethoxycarbonyl, tert-butoxycarbonyl.

The term "aralkyloxy-carbonyl" as used herein includes benzyloxycarbonyl, p-nitrobenzyloxycarbonyl, 9-fluorenyl-methyloxycarbonyl.

The term "lower alkane sulfonyl" as used herein includes methane sulfonyl, ethane sulfonyl; aryl sulfonyl such as toluene sulfonyl.

The term "tri-(lower alkyl) silyl" as used herein includes trimethylsilyl.

In one embodiment, in step a) of the above process, the methylation of compound of formula IV can be achieved by adding a suitable methylation agent to the compound of formula IV. Suitable methylation agents can be selected from the group consisting of dimethyl sulphate, methyl iodide, trimethyl phosphate. Preferably, the methylation agent is methyl iodide.

In one embodiment, methylation may be carried out in presence of a suitable base.

A suitable base may be selected from an organic or an inorganic base. The inorganic base may be selected from the group consisting of hydrides such as sodium hydride, lithium hydride; hydroxides such as sodium hydroxide, potassium hydroxide, calcium hydroxide; alkoxides such as sodium methoxide, potassium methoxide, sodium tert-butoxide, potassium tert-butoxide; carbonates such as sodium carbonate, potassium carbonate; bicarbonates such as sodium bicarbonate, potassium bicarbonate and the like; organic base may be selected from triethyl amine, trimethyl amine, diisopropyl ethylamine, dimethyl amino pyridine, picoline and pyridine. Preferably the base is sodium hydride.

In one embodiment, the above process may be carried out in presence or absence of a solvent.

A suitable solvent may be selected from, but is not limited to halogenated hydrocarbons such as methylene chloride, ethylene chloride, chloroform and carbon tetrachloride; alcohols such as methanol, ethanol, n-propyl alcohol, 2-propanol, tert-butanol; esters such as ethyl acetate, isopropyl acetate and butyl acetate; amides such as formamide, N,N-dimethylformamide, N,N-dimethylacetamide;sulfoxides like dimethyl sulfoxide; nitrile such as acetonitrile, propionitrile; ethers such as diethyl ether, diisopropyl ether, t-butyl methyl ether, 1,4-dioxane, tetrahydrofuran; sulfolane; water; hydrocarbons such as benzene, toluene, cyclohexane, methyl cyclohexane and toluene; ketones such as acetone methyl ethyl ketone, methyl isobutyl ketone and the like; or mixtures thereof Preferably, the solvent is N,N-dimethylformamide In one embodiment, in step b) of the above process, deprotection of compound of formula V is carried out using suitable reagent depending on the type of protective groups $R_1$ and $R_2$.

The deprotection when $R_1$ and $R_2$ together with the nitrogen to which they are attached form a phthalimido group wherein the aromatic ring of the phthalimido group is unsubstituted or substituted with one or more $R_3$ substituents selected from the group consisting of halogen, alkyl, nitro and amino may be carried out using reagents selected from the group consisting of amines, hydrazine and hydrazine hydrate.

The amines for deprotection may be selected from primary amine, secondary amine and tertiary amine which may be unsubstituted or substituted by small functional groups like hydrox, nitro, halo. The amines may be selected from pyridine, piperidine, ammonia, methylamine, ethylamine, ethanolamine and cyclohexyl amine.

The deprotection when $R_1$ is H and $R_2$ is trialkylsilyl or trialkylsilylethoxycarbamates may be carried out using quaternary ammonium compounds such as tetrabutylammonium fluoride in the presence of solvents such as dimethylformamide, tetrahydrofuran and the like, in mildly basic conditions.

The deprotection when $R_1$ is H and $R_2$ is acetyl, trihaloacetyl, alkylsulfonyl, arylsulfonyl, diphenylphosphine, may be carried out using an acid or a base.

The acids used for deprotection may be selected from mineral acids like hydrochloric acid, sulfuric acid, nitric acid or organic acids such as acetic acid, methanesulfonic acid, trifluoroacetic acid, p-toluene sulfonic acid, boron tribromide in methylene dichloride, formic acid and the like.

The base used for deprotection may be selected from inorganic base or organic base. The inorganic base may be selected from the group consisting of alkali metal hydroxides such as sodium hydroxide, potassium hydroxide, barium hydroxide and lithium hydroxide and the like; metal carbonates such as sodium carbonate, potassium carbonate, magnesium carbonate, and calcium carbonate and the like; metal bicarbonates such as sodium bicarbonate, and potassium bicarbonate; metal hydrides such as lithium hydride, sodium hydride, and potassium hydride and the like; borohydrides such as sodium borohydride, potassium borohydride; and bases such as lithium aluminium hydride and ammonia. The organic base may be selected from the group consisting of organic amines such as triethylamine, diisopropylethylamine, N,N-dimethylaniline, pyridine, 4-dimethylaminopyridine, tri-n-butylamine, N-methylmorpholine, piperidine and the like; alkali metal alkoxides such as sodium methoxide, sodium ethoxide, sodium-tert-butoxide, potassium methoxide, potassium ethoxide, potassium-tert-butoxide, lithium methoxide, lithium ethoxide, lithium-tert-butoxide and the like.

The deprotection when $R_1$ is H and $R_2$ is an aralkyloxycarbonyl such as benzyloxycarbonyl, may be carried out using palladium carbon or palladium hydroxide.

The deprotection when $R_1$ is H and $R_2$ is lower alkoxycarbonyl such as, tert-butoxycarbonyl may be carried out using an acid such as hydrochloric acid, phosphoric acid.

The deprotection when $R_1$ is H and $R_2$ is aralkyl such as trityl, may be carried out using mild acids such as trifluoroacetic acid, trichloroacetic acid or by using 1-hydroxy-1-H benzotriazole. The reaction may be carried out in solvent selected from halogenated hydrocarbon or trifluoroethanol or when $R_1$ is H and $R_2$ is aralkyl such as benzyl, deprotection may be carried out using palladium carbon or palladium hydroxide.

The deprotection when $R_1$ is H and $R_2$ is sulfonylethoxycarbonyl, may be carried out using inorganic bases as described above.

The deprotection reaction may be carried out in presence of a solvent or without solvent. Suitable solvent may be selected from the group consisting of water, alcohols such as methanol, ethanol, 1-propanol, 2-propanol, tertiary-butanol; ketones such as acetone, methyl ethyl ketone; nitriles such as acetonitrile, propionitrile; amides such as formamide, N,N-dimethylformamide, N,N-dimethylacetamide, 1,3-dimethyl-2-imidazolidinone; ethers such as diethyl ether, diisopropyl ether, t-butyl methyl ether, 1,4-dioxane, THF (tetrahydrofuran); esters such as ethyl formate, ethyl acetate, propyl acetate; halogenated hydrocarbons such as dichloromethane, chloroform, 1,2-dichloroethane; hydrocarbons such as n-hexane, cyclohexane, benzene, toluene and methyl cyclohexane; sulfoxides such as dimethyl sulfoxide; polar solvents such as sulfolane, hexamethylphosphorylamide; or mixtures thereof. Preferably, the deprotection is carried out in absence of a solvent.

In one embodiment, the present invention provides a process for the preparation of alogliptin, a compound of formula I, or a salt thereof comprising a) methylating a compound of formula IV, to obtain a compound of formula V

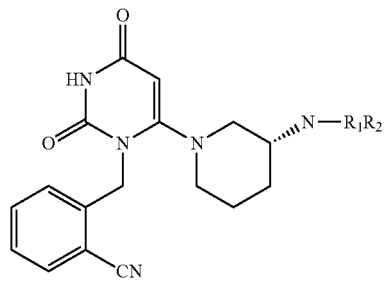

IV

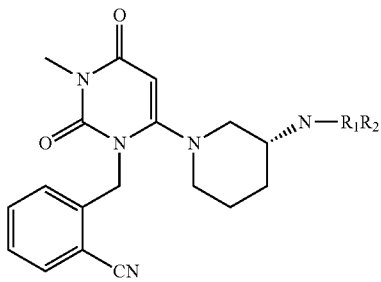

wherein R₁ and R₂ together with the nitrogen to which they are attached form a phthalimido group, wherein the aromatic ring of the phthalimido group is unsubstituted or substituted with one or more $R_3$ substituents selected from the group consisting of halogen, alkyl, nitro and amino; and b) deprotecting the compound of formula V to obtain compound of formula I.

The deprotection of compound of formula V may be carried out using reagents selected from the group consisting of amines, hydrazine and hydrazine hydrate.

In one embodiment, in the above process $R_1$ and $R_2$ together with the nitrogen to which they are attached form a phthalimido group wherein $R_3$ on the aromatic ring of the phthalimido group is alkyl. Preferably, the alkyl is methyl.

In one embodiment the present invention provides a process for the preparation of alogliptin, or a salt thereof comprising:

a) methylating 2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile, a compound of formula IVa to obtain 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl) benzonitrile a compound of formula Va; and

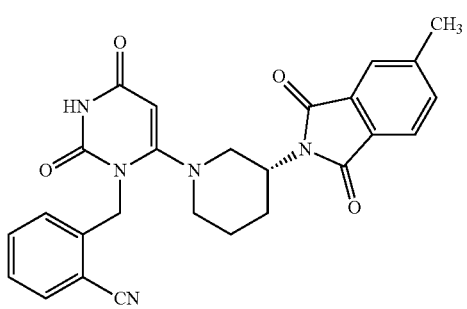

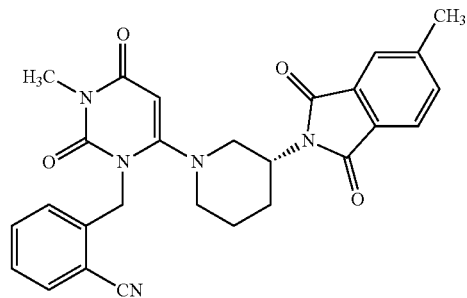

b) deprotecting 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile, the compound of formula Va to obtain alogliptin, a compound of formula I.

In one embodiment, in step a) of the above process, methylation may be carried out using methyl iodide. The reaction may be carried out in a suitable protic solvent such as N,N dimethyl formamide The reaction transpires at a temperature of about −5 to about 40° C. Preferably the reaction transpires at about 25 to about 30° C.

In one embodiment, step b) of the above process compound of formula Va may be deprotected using reagents selected from the group consisting of amines, hydrazine and hydrazine hydrate.

In one embodiment compound of formula Va is deprotected using ethanolamine to obtain a compound of formula I.

The reaction transpires at a temperature of about 20° C. to about reflux temperature. Preferably, the reaction transpires at a temperature of about 60 to about 65° C.

In one embodiment, the present invention provides a process for the preparation of alogliptin, or a salt thereof comprising:

a) methylating a compound of formula IVb to obtain a compound of formula Vb; and

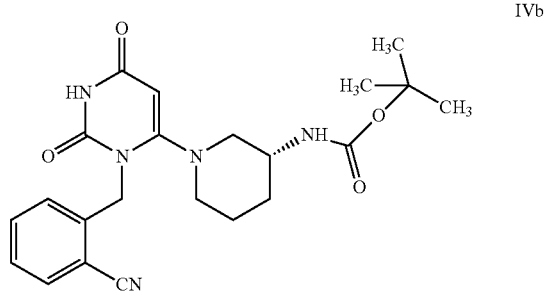

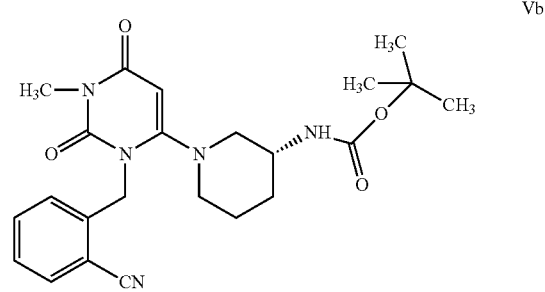

b) deprotecting the compound of formula Vb to obtain alogliptin, a compound of formula I.

In one embodiment, step a) of the above process, methylation may be carried out using methyl iodide.

In one embodiment, step b) of the above process compound of formula Vb may be deprotected using acids such as hydrochloric acid, phosphoric acid. Preferably, the deprotection is carried out using hydrochloric acid.

In one embodiment, the present invention provides a process for the preparation of alogliptin, or a salt thereof comprising:

a) methylating a compound of formula IVc to obtain a compound of formula Vc; and

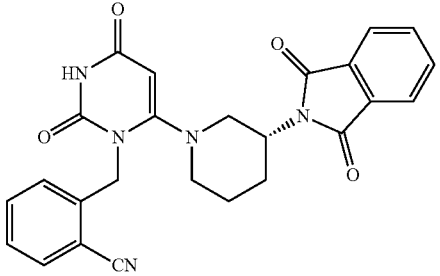

IVc

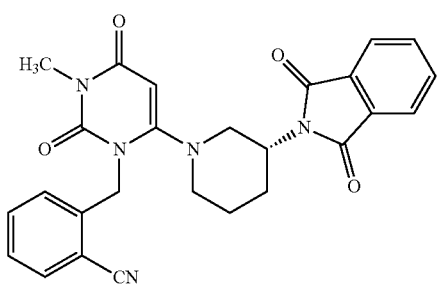

Vc b) deprotecting the compound of formula Vc to obtain alogliptin, a compound of formula I.

In one embodiment, compound of formula I may be converted to a suitable acid addition salt selected from the group consisting of benzoate, mandelate, oxalate, mesylate and acetate.

In one embodiment, the present invention provides a compound of formula IV, or stereoisomer thereof

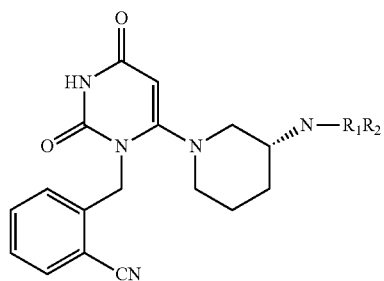

IV wherein R₁ and R₂ are as defined earlier.

In one embodiment, the present invention provides a compound of formula IV, wherein R₁ and R₂ together with the nitrogen to which they are attached form a phthalimido group wherein the aromatic ring of the phthalimido group is unsubstituted or substituted with one or more R₃ substituent selected from the group consisting of halogen, alkyl, nitro and amino.

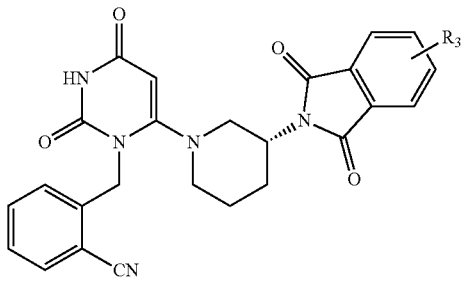

In one embodiment, the present invention provides a compound of formula IV wherein R₁ and R₂ together with the nitrogen to which they are attached form a phthalimido group and wherein R₃ on the aromatic ring of the phthalimido group is alkyl.

In one embodiment, the present invention provides 2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile a compound of formula IVa.

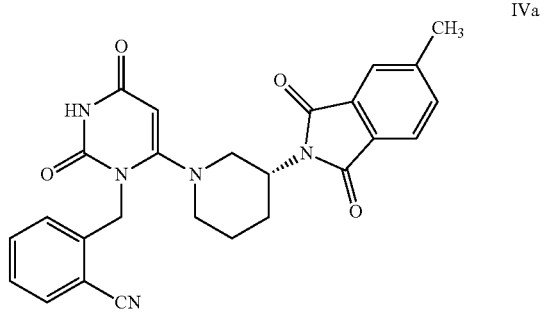 [SMILES: Cc1ccc2c(c1)C(=O)N([C@@H]1CCCN(c3cc(=O)[nH]c(=O)n3Cc3ccccc3C#N)C1)C2=O]

IVa

In one embodiment, the present invention provides compound of formula IVa, characterized by a proton NMR spectrum having peaks at about δ 8.87 (s,1H), 7.60-7.68 (dd,2H), 7.60 (s,1H), 7.4-7.57 (dd,2H), 7.39 (s,1H), 7.17-7.19 (dd,1H), 5.33-5.35 (s,1H), 5.16-5.21(d,2H), 4.24 (s,1H), 3.40(s,1H), 2.96-2.99 (d,1H) 2.50 (s,1H), 2.34-2.40 (dd,2H) ,1.73-1.90(dd,6H).

Proton NMR spectra were recorded in CDCl₃ or DMSO-d₆ using NMR instrument-Varian 300 MHZ.

In one embodiment, the present invention provides a compound of formula IVb.

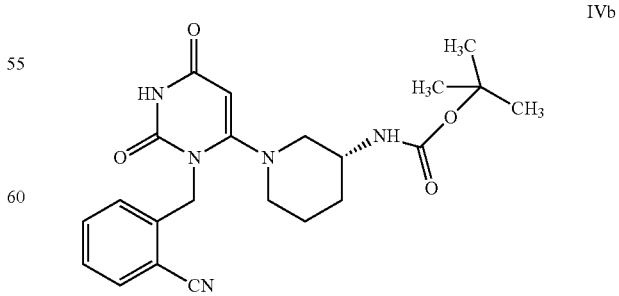

IVb

In one embodiment, the present invention provides a compound of formula IVc.

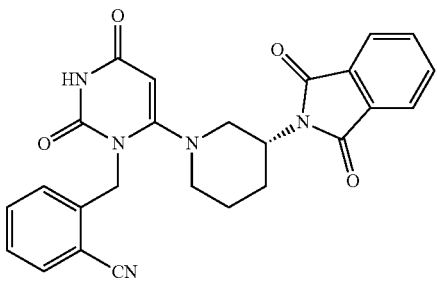

IVc

In one embodiment, the present invention provides a process for the preparation of compound of formula IV comprising reacting a compound of formula II with a compound of formula III

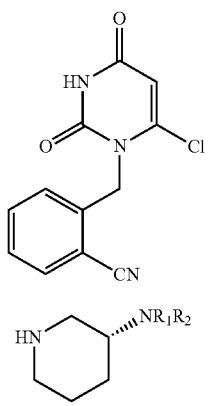

II

III wherein $R_1$ and $R_2$ are as defined earlier.

In one embodiment, the present invention provides a process for the preparation of compound of formula IVa comprising reacting a compound of formula II with 5-methyl-2-[(3R)-piperidin-3-yl]-2,3-dihydro-1H-isoindole-1,3-dione, a compound of formula IIIa.

In one embodiment, compound of formula II is reacted with a compound of formula IIIa in the presence of a suitable base and a suitable solvent.

A suitable solvent may be selected from, but is not limited to halogenated hydrocarbons such as methylene chloride, ethylene chloride, chloroform and carbon tetrachloride; alcohols such as methanol, ethanol, n-propyl alcohol, 2-propanol, tert-butanol; esters such as ethyl acetate, isopropyl acetate and butyl acetate; amides such as formamide, N,N-dimethylformamide, dimethyl sulfoxide, N,N-dimethylacetamide; nitrile such as acetonitrile, propionitrile; ethers such as diethyl ether, diisopropyl ether, t-butyl methyl ether, 1,4-dioxane, tetrahydrofuran; sulfolane; water; hydrocarbons such as benzene, toluene, cyclohexane, methyl cyclohexane and toluene; ketones such as acetone methyl ethyl ketone, methyl isobutyl ketone and the like; or mixtures thereof. Preferably, the solvent is methanol A suitable base may be selected from an organic or an inorganic base. The inorganic base may be selected from the group consisting of hydrides such as sodium hydride, lithium hydride, hydroxides such as sodium hydroxide, potassium hydroxide, calcium hydroxide; alkoxides such as sodium methoxide, potassium methoxide, sodium tert-butoxide, potassium tert-butoxide; carbonates such as sodium carbonate, potassium carbonate; bicarbonates such as sodium bicarbonate, potassium bicarbonate and the like; organic base may be selected from triethyl amine, trimethyl amine, diisopropyl ethylamine, dimethyl amino pyridine, picoline, and pyridine. Preferably the base is potassium carbonate.

In a one embodiment, the present invention provides a process for the preparation of compound of formula IVb comprising reacting a compound of formula II with a compound of formula IIIb in the presence of methanol and potassium carbonate.

The reaction transpires at a temperature of about 15° C. to about reflux temperature of the solvent. Preferably, the reaction transpires at about reflux temperature of the solvent.

In another embodiment, the present invention provides a process for the preparation of compound of formula IVb comprising reacting a compound of formula II with a compound of formula IIIb.

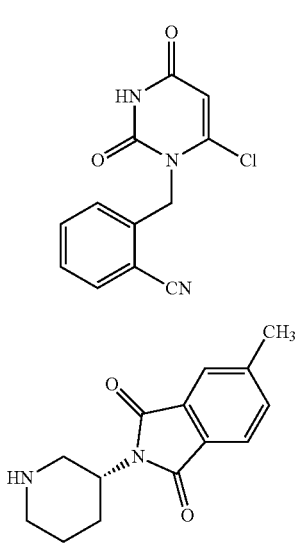

II

IIIa

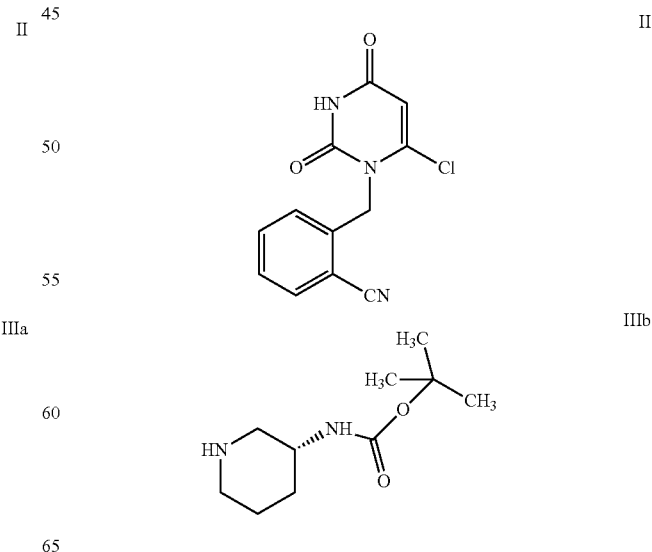

II

IIIb

The compound of formula II, can be made by any method known in the art.

In one embodiment, the present invention provides a process for the preparation of alogliptin or a salt thereof comprising deprotecting a compound of formula V

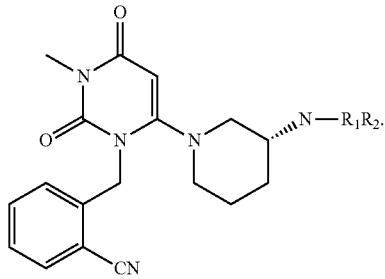

wherein $R_1$ and $R_2$ together with the nitrogen to which they are attached form a phthalimido group, wherein the aromatic ring of the phthalimido group is unsubstituted or substituted with one or more $R_3$ substituents selected from the group consisting of halogen, alkyl, nitro and amino; or $R_1$ is H and $R_2$ is an amino protecting group selected from the group consisting of aralkyl, acyl, lower alkoxy-carbonyl, aralkyloxy-carbonyl, lower alkane sulfonyl, aryl sulfonyl, tri-(lower alkyl) silyl, 2-trialkylsilylethoxycarbamates, triphosgene, diphenylphosphine and sulfonylethoxycarbonyl.

The deprotection depending on the type of protection may be carried out using suitable reagents.

A suitable deprotecting reagent may be selected from the group consisting of hydrazine, hydrazine hydrate, amines such as primary amine, secondary amine and tertiary amine which may be unsubstituted or substituted by small functional groups like hydroxy, nitro, halo such as pyridine, piperidine, ammonia, methylamine, ethanolamine and cyclohexyl amine; quaternary ammonium compounds such as tetrabutylammonium fluoride; acids selected from organic or inorganic acid such as hydrochloric acid, sulfuric acid, nitric acid, phosphoric acid, trifluroacetic acid, trichloroacteic acid, acetic acid, methanesulfonic acid, trifluoroacetic acid, p-toluene sulfonic acid, boron tribromide in methylenedichloride, formic acid and the like; base used for deprotection may be selected from inorganic base or organic base such as morpholine, piperazine, sodium hydride and the like. The deprotection depending on type of protecting group may also be carried out using palladium carbon or palladium hydroxide.

In one embodiment, the present invention provides a process for the preparation of alogliptin or a salt thereof comprising deprotecting 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile the compound of formula Va to obtain alogliptin, a compound of formula I.

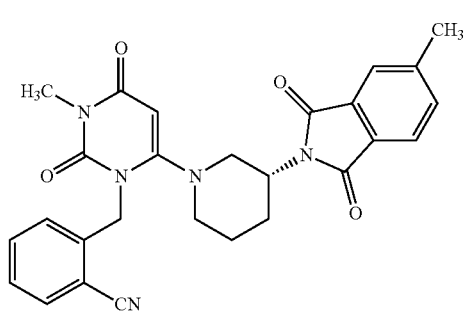

The deprotection may be carried out using suitable deprotecting reagent selected from the group consisting of hydrazine, hydrazine hydrate, amines such as primary amine, secondary amine and tertiary amine which may be unsubstituted or substituted by small functional groups like hydroxy, nitro, halo such as pyridine, piperidine, ammonia, methylamine, ethanolamine and cyclohexyl amine;

In one embodiment, the present invention provides alogliptin, compound of formula I as an oil, oily mass, residue or a semisolid.

In one embodiment, the present invention provides alogliptin, in non-crystalline Form.

In one embodiment, the present invention provides a process for the preparation of alogliptin benzoate from a compound of formula V without isolating, alogliptin, compound of formula I.

In one embodiment, the present invention provides a process for the preparation of alogliptin benzoate comprising deprotecting compound of formula Va to obtain a compound I and converting compound of formula I to alogliptin benzoate, without isolating compound of formula I.

In one embodiment, the compound of formula Va is deprotected using ethanolamine to obtain alogliptin base insitu and then treated with benzoic acid to obtain alogliptin benzoate.

In one embodiment the present invention provides 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile, compound of formula Va.

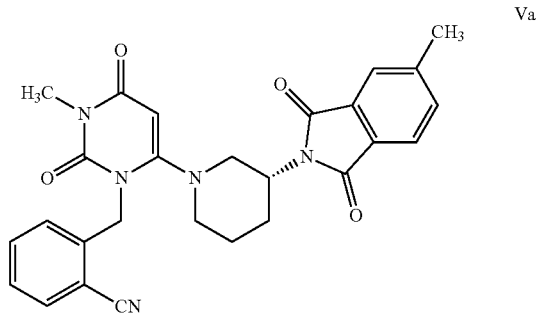 [SMILES: Cc1ccc2c(c1)C(=O)N([C@@H]1CCCN(c3cc(=O)n(C)c(=O)n3Cc3ccccc3C#N)C1)C2=O]

In one embodiment, the present invention provides compound of formula Va, characterized by a proton NMR spectrum having peaks at about $^1$H NMR (300 MHz in CDCl$_3$): δ 8.01(s,1H), 7.68-7.62 (d,2H), 7.34-7.57 (dd,3H), 7.13-7.16 (d,1H), 5.42 (s,1H), 5.26-5.33(dd,2H), 3.30(s,3H), 2.96(s,1H),2.65-2.72 (t,1H) 2.51 (s,2H), 2.41 (s,1H),1.70 (s,7H)

In one embodiment, the present invention provides a process for the preparation of alogliptin benzoate comprising
 (a) treating alogliptin with an acid to form an acid addition salt of alogliptin; and
 (b) treating the acid addition salt of alogliptin with a base, followed by addition of benzoic acid to obtain alogliptin benzoate.

The acid addition salt may be selected from the group consisting of hydrochloric acid, sulfuric acid, nitric acid, phosphoric acid, methanesulfonic acid, acetic acid, trifluoroacetic acid, citric acid, maleic acid, and succinic acid.

The base may be selected from an organic or an inorganic base as described supra.

In one embodiment, the present invention provides a process for the preparation of alogliptin benzoate comprising
(a) treating alogliptin with acetic acid to form alogliptin acetate; and
(b) treating the alogliptin acetate with a base, followed by addition of benzoic acid to obtain alogliptin benzoate.

In one embodiment, the present invention provides conversion of alogliptin trifluroacetate to alogliptin benzoate.

In one embodiment, the present invention provides conversion of alogliptin mesylate to alogliptin benzoate.

In one embodiment, the present invention provides a process for the preparation of crystalline form A of alogliptin benzoate comprising
(a) treating alogliptin with benzoic acid to form alogliptin benzoate; and
(b) subjecting the alogliptin benzoate to slurrying in a solvent system selected from the group consisting of n-propanol, hexane, ethylene dichloride, methyl tertiary butyl ether, xylene, methyl tetrahydrofuran, propyl acetate, methyl acetate or mixtures thereof or mixture with water.

In one embodiment, the present invention provides process for the preparation of crystalline form A of alogliptin benzoate comprising isolating alogliptin benzoate from a solvent selected from the group consisting of n-propanol, hexane, ethylene dichloride, methyl tertiary butyl ether, xylene, methyl tetrahydrofuran, propyl acetate, methyl acetate or mixtures thereof.

In one embodiment, the isolation of crystalline form A of alogliptin benzoate comprises a) subjecting alogliptin benzoate to slurrying in a solvent selected from the group consisting of n-propanol, hexane, ethylene dichloride, methyl tertiary butyl ether, xylene, methyl tetrahydrofuran, propyl acetate, methyl acetate or mixtures thereof to obtain solid alogliptin benzoate; and b) filtering out the solid alogliptin benzoate.

In one embodiment, the isolation of crystalline form A of alogliptin benzoate comprises a) subjecting alogliptin benzoate to slurrying in a solvent selected from the group consisting of n-propanol, propyl acetate, methyl acetate or mixtures thereof to obtain solid alogliptin benzoate; and b) filtering out the solid alogliptin benzoate. The slurrying may be carried out at room temperature.

In one embodiment, the isolation of crystalline form A of alogliptin benzoate comprises stirring the crude alogliptin benzoate obtained as a residue, oil or sticky mass from an earlier reaction in a solvent selected from the group consisting of n-propanol, hexane, ethylene dichloride, methyl tertiary butyl ether, xylene, methyl tetrahydrofuran, propyl acetate, methyl acetate or mixtures thereof to obtain solid alogliptin benzoate; and b) filtering out the solid alogliptin benzoate.

In one embodiment, the isolation of crystalline form A of alogliptin benzoate comprises subjecting alogliptin benzoate to recrystallization in a solvent selected from the group consisting of n-propanol, hexane, ethylene dichloride, methyl tertiary butyl ether, xylene, methyl tetrahydrofuran, propyl acetate, methyl acetate or mixtures thereof .The recrystallization may be carried out at room temperature or at higher temperatures.

In one embodiment, the present invention provides a process for the preparation of crystalline form A of alogliptin benzoate comprising recrystallizing alogliptin benzoate from n-propanol.

In one embodiment, the present invention provides process for the preparation of crystalline form of alogliptin benzoate characterized by X-ray diffraction (XRD) spectrum having peak reflections at about 9.35, 10.74, 17.73, 18.65, 25.79, 28.42±0.2 degrees 2 theta comprising slurrying alogliptin benzoate in n-propanol.

In one embodiment, the present invention provides alogliptin benzoate having chiral purity greater than 99.98% as determined by HPLC.

In one embodiment, the present invention provides alogliptin benzoate having a chemical purity of at least 99.6% and chiral purity of 99.95% as determined by HPLC In one embodiment, the present invention provides alogliptin benzoate having chemical purity greater than 99.6% and chiral purity greater than 99.98% as determined by HPLC.

In one embodiment, the present invention provides alogliptin benzoate having chemical purity greater than 99.6% and wherein the level of 2-({6-[(3S)-3-aminopiperidin-1-yl]-3-methyl-2,4-dioxo-3,4-dihydropyrimidin-1(2H)-yl}methyl)benzonitrile benzoate is below 0.05%.

In one embodiment, the present invention provides alogliptin benzoate having a $d_{90}$ particle size of less than 200 µm.

In one embodiment, the present invention provides alogliptin benzoate with $d_{90}$ particle size of about 160 microns, $d_{50}$ about 58 microns and $d_{10}$ of about 1.5 microns.

In one embodiment the present invention provides use of compound of formula IV or V in the preparation of the compound of formula I or its salt thereof.

In one embodiment, the present invention provides use of compound of formula IVa in the preparation of alogliptin, a compound of formula I or its salt thereof.

In one embodiment, the present invention provides use of compound of formula IVb in the preparation of alogliptin, a compound of formula I or its salt thereof.

In one embodiment, the present invention provides use of compound of formula IVc in the preparation of alogliptin, a compound of formula I or its salt thereof.

In one embodiment the present invention provides use of compound of formula V in the preparation of the compound of formula I or its salt thereof.

In one embodiment the present invention provides use of compound of formula Va in the preparation of the compound of formula I or its salt thereof.

In one embodiment the present invention provides use of compound of formula Vb in the preparation of the compound of formula I or its salt thereof.

The following examples are provided to enable one skilled in the art to practice the invention and are merely illustrative of the invention. The examples should not be read as limiting the scope of the invention as defined in the features and advantages.

EXAMPLES

Example 1

2-[(6-chloro-2,4-dioxo-1,2,3,4-tetrahydropyrimidin-1-yl)methyl]benzonitrile: Compound of Formula II A mixture of 6-chlorouracil (2.0 gm) in dimethyl formamide (15 ml) and dimethyl sulfoxide (15 ml) was stirred at about 25° C. to get a clear solution. The reaction mass was cooled to about 0 to about 5° C. and sodium hydride (0.8 gm) was added slowly. The reaction mass was further stirred at 0 to about 5° C. for about 1 h. To the reaction mass, a solution of 2-cyano benzyl bromide (2.3 gm) in dimethyl formamide (10 ml) was added drop wise while maintaining temperature at about 0 to about 5° C. The reaction mass was further stirred for 3 to 4 h at 25-30° C. and water (100 ml) was charged to the reaction mass to give white precipitate which was filtered & dried to give 2.0 gm of title compound. MS (ESI)[m+H] found 262.15.

Example 2

2-[(6-chloro-2,4-dioxo-1,2,3,4-tetrahydropyrimidin-1-yl)methyl]benzonitrile: Compound of Formula II A mixture of 6-chlorouracil (2.0 gm) in dimethyl sulfoxide (16 ml) was stirred at about 25° C. to get a clear solution and potassium carbonate (0.94 gm) was added. The reaction mass was further stirred at 20 to 25° C. for about 1 hr. To the reaction mass, a solution of 2-cyano benzyl bromide (2.94 gm) in dimethyl sulfoxide (4.0 ml) was added drop wise and reaction mass was further stirred for 1 to 2 h at 25-30° C. and water (80 ml) was added to the reaction mass which was purified with DMF (6.0 ml) to give white precipitate which was filtered & dried to give 1.0 gm of title compound. Purity 95.0%-99.0%

Example 3

2-[(6-chloro-2,4-dioxo-1,2,3,4-tetrahydropyrimidin-1-yl) methyl]benzonitrile: Compound of Formula II A mixture of 6-chlorouracil (2.0 gm) in tetrahydrofuran (20 ml) was stirred at about 25° C. to get a clear solution and potassium carbonate (0.94 gm) was added. The reaction mass was further stirred at 20 to 25° C. for about 1 hr. To the reaction mass, a solution of 2-cyano benzyl bromide (2.94 gm) in tetrahydrofuran (4.0 ml) was added drop wise and reaction mass was further stirred for 1 to 2 h at 25-30° C. and water (80 ml) was added to the reaction mass which was purified with DMF to give white precipitate which was filtered & dried to give 1.0 gm of title compound.

Example 4

2-[(6-chloro-2,4-dioxo-1,2,3,4-tetrahydro pyrimidin-1-yl) methyl]benzonitrile: Compound of Formula II A mixture of 6-chlorouracil (2.0 gm) in tetrahydrofuran (10 ml) and dimethyl sulphoxide (10 ml) was stirred at about 25° C. to get a clear solution and potassium carbonate (0.94 gm) was added. The reaction mass was further stirred at 20 to 25° C. for about 1 hr. To the reaction mass, a solution of 2-cyano benzyl bromide (2.94 gm) in tetrahydrofuran (4.0 ml) was added drop wise and reaction mass was further stirred for 1 to 2 h at 25-30° C. and water (80 ml) was added to the reaction mass which was purified with DMF to give white precipitate which was filtered & dried to give 1.0 gm of title compound.

Example 5

2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula IVa A mixture of 2-[(6-chloro-2,4-dioxo-1,2,3,4-tetrahydropyrimidin-1-yl)methyl]benzonitrile(1.0 gm) and 5-methyl-2-[(3R)-piperidin-3-yl]-2,3-dihydro-1H-isoindole-1,3-dione (0.75 gm) in methanol (10 ml) was stirred for 10 min Potassium carbonate (1 gm) was charged to the reaction mass and heated to reflux for 6 to 12 h. The reaction mass was cooled to 25° C. and water was charged to the reaction mass to give white precipitate which was filtered and dried to give 0.6 gm of title compound. MS (ESI)[m+H] found 470.42.

Example 6

2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula IVa A mixture of 2-[(6-chloro-2,4-dioxo-1,2,3,4-tetrahydropyrimidin-1-yl)methyl]benzonitrile(2.0 gm) and 5-methyl-2-[(3R)-piperidin-3-yl]-2,3-dihydro-1H-isoindole-1,3-dione (1.05 gm) in dimethylsulphoxide (20 ml) was stirred for 10 min Potassium carbonate (2.1 gm) was charged to the reaction mass and heated to 50-60° C. for 6 to 10 hr. The reaction mass was cooled to 15-25° C. and aqueous hydrochloric acid solution was added to the reaction mass to give white precipitate which was filtered and purified in Acetone: water, dried to give 3.2 gm of title compound. MS (ESI) [m+H] found 470.42. Purity 90.0%-95.0%.
$^1$H NMR (300 MHz in CDCl$_3$): δ 8.87 (s,1H), 7.60-7.68 (dd,2H), 7.60 (s,1H), 7.4-7.57 (dd,2H), 7.39 (s,1H), 7.17-7.19 (dd,1H), 5.33-5.35 (s,1H), 5.16-5.21(d,2H), 4.24 (s,1H), 3.40(s,1H), 2.96-2.99 (d,1H) 2.50 (s,1H), 2.34-2.40 (dd,2H) ,1.73-1.90(dd,6H)

Example 7

2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula IVa A mixture of 2-[(6-chloro-2,4-dioxo-1,2,3,4-tetrahydropyrimidin-1-yl)methyl]benzonitrile(2.0 gm) and 5-methyl-2-[(3R)-piperidin-3-yl]-2,3-dihydro-1H-isoindole-1,3-dione (1.05 gm) in dimethylsulphoxide (20 ml) was stirred for 10 min Disopropylethyl amine (4.0 gm) was added to the reaction mass and heated to 50-60° C. for 6 to 10 hr. The reaction mass was cooled to 15-25° C. and aqueous hydrochloric acid solution was added to the reaction mass to give a white precipitate which was filtered and purified in acetone:water , dried to give 3.2 gm of title compound. MS (ESI) [m+H] found 470.42.

Example 8

2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula IVa A mixture of 2-[(6-chloro-2,4-dioxo-1,2,3,4-tetrahydropyrimidin-1-yl)methyl]benzonitrile(2.0 gm) and 5-methyl-2-[(3R)-piperidin-3-yl]-2,3-dihydro-1H-i soindole-1,3-dione (1.05 gm) in N-methylpyrolidone (20 ml) was stirred for 10 min Potassium carbonate (2.1gm) was charged to the reaction mass and heated to 50-60° C. for 6 to 10 hr. The reaction mass was cooled to 15-25° C. and aqueous hydrochloric acid solution was added to the reaction mass to give white precipitate which was filtered and purified in acetone: water, dried to give 3.2 gm of title compound. MS (ESI) [m+H] found 470.42.

Example 9

2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula IVa A mixture of 2-[(6-chloro-2,4-dioxo-1,2,3,4-tetrahydropyrimidin-1-yl)methyl]benzonitrile(2.0 gm) and 5-methyl-2-[(3R)-piperidin-3-yl]-2,3-dihydro-1H-isoindole-1,3-dione (1.05 gm) in N-methylpyrolidone (20 ml) was stirred for 10 min Disopropylethyl amine (4.0 gm) was charged to the reaction mass and heated to 50-60° C. for 6 to 10 hr. The reaction mass was cooled to 15-25° C. and aqueous hydrochloric acid solution was added to the reaction mass to give white precipitate which was filtered and purified in acetone: water, dried to give 3.2 gm of title compound. MS (ESI) [m+H] found 470.42.

Example 10

2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula IVa A mixture of 2-[(6-chloro-2,4-dioxo-1,2,3,4-tetrahydropyrimidin-1-yl)methyl]benzonitrile(2.0 gm) and 5-methyl-2-[(3R)-piperidin-3-yl]-2,3-dihydro-1H-isoindole-1,3-dione (1.05 gm) in acetonitrile (20 ml) was stirred for 10 min Disopropylethyl amine (4.0 gm) was charged to the reaction mass and heated to 50-60° C. for 6 to 10 hr. The reaction mass was cooled to 15-25° C. and aqueous hydrochloric acid solution (50 ml) was added to the reaction mass to give white precipitate which was filtered and purified in acetone: water, dried to give 3.2 gm of title compound. MS (ESI) [m+H] found 470.42.

Example 11

2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula IVa A mixture of 2-[(6-chloro-2,4-dioxo-1,2,3,4-tetrahydropyrimidin-1-yl)methyl]benzonitrile(2.0 gm) and 5-methyl-2-[(3R)-piperidin-3-yl]-2,3-dihydro-1H-isoindole-1,3-dione (1.05 gm) in dimethylformamide was stirred for 10 min Disopropylethyl amine (4.0 gm) was added to the reaction mass and heated to 50-60° C. for 6 to 10 hr. The reaction mass was cooled to 15-25° C. and aqueous hydrochloric acid solution (50 ml) was added to the reaction mass to give white precipitate which was filtered and purified in acetone: water, dried to give 3.2 gm of title compound. MS (ESI) [m+H] found 470.42.

Example 12

2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula IVa A mixture of 2-[(6-chloro-2,4-dioxo-1,2,3,4-tetrahydropyrimidin-1-yl)methyl]benzonitrile(2.0 gm) and 5-methyl-2-[(3R)-piperidin-3-yl]-2,3-dihydro-1H-isoindole-1,3-dione (1.05 gm) in dimethylformamide (20 ml) was stirred for 10 min Potassium carbonate (2.1gm) was added to the reaction mass and heated to 50-60° C. for 6 to 10 hr. The reaction mass was cooled to 15-25° C. and aqueous hydrochloric acid solution (50 ml) was added to the reaction mass to give white precipitate which was filtered and purified in acetone: water, dried to give 3.2 gm of title compound. MS (ESI) [m+H] found 470.42.

Example 13

2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula Va A mixture of 2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile(2.0 gm) in dimethyl formamide (20 ml) was stirred for 5.0 minutes and sodium hydride (0.1 gm) was added at about 0° C. The reaction mass was further stirred for 30 min at 0-5° C. and methyl iodide (0.2 gm) was added. The reaction mass was further stirred at 25-30° C. for 1 to 2 h. The reaction mass was cooled to 25° C. and water was charged to the reaction mass to give white precipitate which was filtered & dried to give 0.6 gm of title compound.

Example 14

2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula Va A mixture of 2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile(2.0 gm) in dimethyl formamide (20 ml) was stirred for 5.0 minutes and potassium carbonate (1.18 gm) was added at about 25-30° C. The reaction mass was further stirred for 30 min at 25-30° C. and methyl iodide (0.2 gm) was added at 25-30° C. The reaction mass was further stirred at 50-55° C. for 1 to 2 h. The reaction mass was cooled to 25° C. and water was charged to the reaction mass to give white precipitate which was filtered & dried to give 1.4 gm of title compound MS (ESI) [m+H] found 483.5.

Example 15

2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula Va A mixture of 2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile(2.0 gm) in acetone (20 ml) was stirred for 5.0 minutes and potassium carbonate (1.18 gm) was added at about 25-30° C. The reaction mass was further stirred for 30 min at 25-30° C. and methyl iodide (0.7 gm) was added at 25-30° C. The reaction mass was further stirred at 50-55° C. for 1 to 2 h. The reaction mass was cooled to 25° C. and water was charged to the reaction mass to give white precipitate which was filtered & dried to give 1.6 gm of title compound MS (ESI) [m+H] found 483.5 Purity more than 99.0%.

$^1$H NMR (300 MHz in CDCl$_3$): δ 8.01(s,1H), 7.68-7.62 (d,2H), 7.34-7.57 (dd,3H), 7.13-7.16 (d,1H), 5.42 (s,1H), 5.26-5.33(dd,2H), 3.30(s,3H), 2.96(s,1H),2.65-2.72 (t,1H) 2.51 (s,2H), 2.41 (s,1H),1.70 (s,7H)

Example 16

2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile: compound of formula Va A mixture of 2-({6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile(2.0 gm) in acetone (20 ml) was stirred for 5.0 minutes and potassium carbonate (1.18 gm) was added at about 25-30° C. The reaction mass was further stirred for 30 min at 25-30° C. and methyl iodide (0.7 gm) was added at 25-30° C. The reaction mass was further stirred at 50-55° C. for 1 to 2 h. The reaction mass was cooled to 25° C. and water was added to the reaction mass to give white precipitate which was filtered and purified in acetone. It was dried to give 1.5 gm of title compound MS (ESI) [m+H] found 483.5

Example 17

2-({6-[(3R)-3-aminopiperidin-1-yl]-3-methyl-2,4-dioxo-1,2,3,4-tetrahydropyrimidin-1-yl}methyl)benzonitrile: compound of formula I A mixture of 2-({3-methyl-6-[(3R)-3-(5-methyl-1,3-dioxo-2,3-dihydro-1H- isoindol-2-yl)piperidin-1-yl]-2,4-dioxo-1,2,3,4-tetrahydropyrimidin-1-yl}methyl)benzonitrile (0.5) gm in ethanol amine (50 ml) was stirred at 60 to 65° C. for a period of about 12 to 18 h. The reaction mixture was evaporated under vacuum. To the residue water was added and the product was extracted in dichloromethane. The solvent was evaporated under reduced pressure to give the title compound.

Example 18

2-({6-[(3R)-3-aminopiperidin-1-yl]-3-methyl-2,4-dioxo-1,2,3,4-tetrahydropyrimidin-1-yl}methyl)benzonitrile benzoate A mixture of 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile (2.0) gm in ethanol amine (10 ml) was stirred at 60 to 65° C. for a period of about 8 to 10 h. The reaction mixture was evaporated under vacuum. To the residue water was added and the product was extracted in dichloromethane Separated layers and adjusted pH=1 to 2 using acetic acid solution (20.0 ml). Separated layers and adjusted pH=7 to 9 using 15.0% sodium carbonate solution (30.0 ml) to aqueous layer. Benzoic acid (0.6 g) was added to the organic layer. The solvent was evaporated under reduced pressure and n-propanol was added to this residue and stirred at 25-30° C. The solid obtained was filtered & dried to give 1.1 gm of title compound. HPLC Purity more than 99. 87%.

| Sr. No. | Impurity | Structure |
|---|---|---|
| 1. | 2-({6-[(3R)-3-aminopiperidin-1-yl]-2,4-dioxo-3,4-dihydropyrimidin-1(2H)-yl}methyl)benzonitrile | 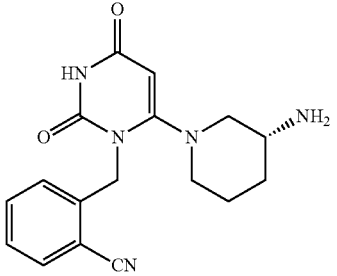 [SMILES: N#Cc1ccccc1Cn1c(N2CCC[C@@H](N)C2)cc(=O)[nH]c1=O] |
| 2. | 3-({6-[(3R)-3-aminopiperidin-1-yl]-3-methyl-2,4-dioxo-3,4-dihydropyrimidin-1(2H)-yl}methyl)benzonitrile benzoate | 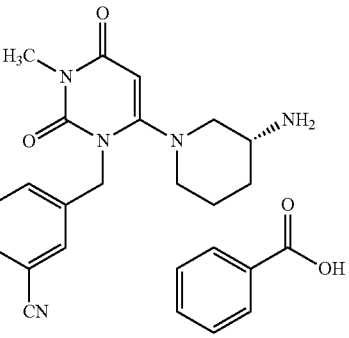 |

| Sr. No. | Impurity | Structure |
|---|---|---|
| 3. | 4-methylbenzene-1,2-dicarboxylic acid | 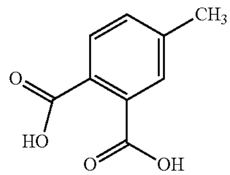 |
| 4. | 4-({6-[(3R)-3-aminopiperidin-1-yl]-3-methyl-2,4-dioxo-3,4-dihydropyrimidin-1(2H)-yl}methyl)benzonitrile benzoate | 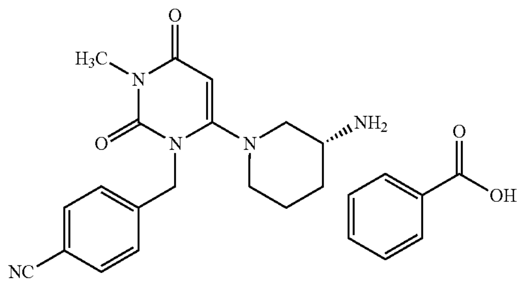 |
| 5. | 2-({6-[(3S)-3-aminopiperidin-1-yl]-3-methyl-2,4-dioxo-3,4-dihydropyrimidin-1(2H)-yl}methyl)benzonitrile benzoate | 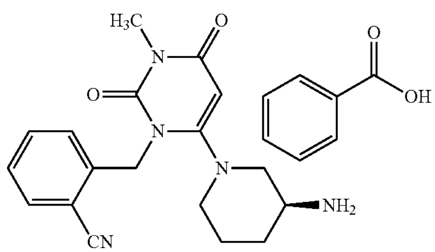 |

The compounds of Formula II, IIIa, IVa, Va and above listed impurities were below detection limit (less than 0.01%) in the title compound.

XRD table of 2-({6-[(3R)-3-aminopiperidin-1-yl]-3-methyl-2,4-dioxo-1,2,3,4-tetrahydropyrimidin-1-yl}methyl)benzonitrile benzoate

| Pos. [°2Th.] | Rel. Int. [%] |
|---|---|
| 9.35 | 49.33 |
| 10.74 | 26.36 |
| 11.25 | 14.29 |
| 12.44 | 14.50 |
| 12.76 | 3.81 |
| 14.01 | 7.84 |
| 14.19 | 6.99 |
| 14.34 | 5.28 |
| 15.12 | 26.39 |
| 16.34 | 1.84 |
| 16.77 | 4.39 |
| 17.73 | 35.79 |
| 18.65 | 100.00 |
| 18.82 | 32.40 |
| 20.04 | 13.92 |
| 20.83 | 72.45 |
| 21.09 | 41.46 |
| 21.78 | 34.96 |
| 22.00 | 12.52 |
| 22.83 | 7.18 |
| 23.19 | 9.07 |
| 23.55 | 16.23 |
| 23.75 | 10.01 |
| 24.36 | 7.98 |
| 25.79 | 12.87 |
| 26.72 | 13.78 |
| 27.00 | 18.25 |
| 27.54 | 9.01 |
| 27.96 | 8.56 |
| 28.42 | 15.28 |
| 28.96 | 10.26 |
| 29.18 | 6.35 |
| 29.65 | 5.80 |
| 30.48 | 1.87 |
| 31.58 | 2.49 |
| 32.11 | 0.90 |
| 32.95 | 1.46 |
| 34.33 | 7.77 |
| 35.00 | 6.34 |
| 35.37 | 4.75 |
| 36.06 | 2.92 |
| 37.72 | 5.30 |
| 38.23 | 6.01 |
| 38.99 | 0.65 |
| 40.73 | 2.59 |
| 42.26 | 0.85 |
| 42.97 | 1.66 |
| 43.75 | 1.61 |
| 44.51 | 2.16 |
| 45.44 | 2.03 |
| 46.39 | 1.58 |
| 47.15 | 2.03 |
| 48.12 | 1.65 |
| 49.39 | 1.62 |

Example 19

2-({6-[(3R)-3-aminopiperidin-1-yl]-3-methyl-2,4-dioxo-1,2,3,4-tetrahydropyrimidin-1-yl}methyl)benzonitrile: benzoate A mixture of 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile (2.0) gm in ethanol amine (10 ml) was stirred at 60 to 65° C. for a period of about 8 to 10 h. The reaction mixture was evaporated under vacuum. To the residue water was added and the product was extracted in dichloromethane. Benzoic acid (0.6 g) was added to the organic layer. The solvent was evaporated under reduced pressure and n-propanol was added to this residue and stirred at 25-30° C. The solid obtained was filtered & dried to give 1.1 gm of title compound.

Example 20

2-({6-[(3R)-3-aminopiperidin-1-yl]-3-methyl-2,4-dioxo-1,2,3,4-tetrahydropyrimidin-1-yl}methyl)benzonitrile: benzoate A mixture of 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile (2.0) gm in mixture of ethanol amine (4 ml) and Toluene (20 ml) was stirred at 60 to 65° C. for a period of about 8 to 10 h. The reaction mixture was evaporated under vacuum. To the residue water was added and the product was extracted in dichloromethane Benzoic acid (0.6 g) was added to the organic layer. The solvent was evaporated under reduced pressure and n-propanol was added to this residue and stirred at 25-30° C. The solid obtained was filtered & dried to give 1.35 gm of title compound.

Example 21

2-({6-[(3R)-3-aminopiperidin-1-yl]-3-methyl-2,4-dioxo-1,2,3,4-tetrahydropyrimidin-1-yl}methyl)benzonitrile: benzoate A mixture of 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile (2.0) gm in mixture of ethanol amine (4 ml) and methanol (20 ml) was stirred at 50 to 65° C. for a period of about 8 to 10 h. The reaction mixture was evaporated under vacuum. To the residue water was added and the product was extracted in dichloromethane (100.0 ml). Benzoic acid (0.6 g) was added to the organic layer. The solvent was evaporated under reduced pressure and n-propanol was added to this residue and stirred at 25-30° C. The solid obtained was filtered & dried to give 1.35 gm of title compound.

Example 22

2-({6-[(3R)-3-aminopiperidin-1-yl]-3-methyl-2,4-dioxo-1,2,3,4-tetrahydropyrimidin-1-yl}methyl)benzonitrile benzoate A mixture of 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile (2.0) gm in mixture of ethanol amine (4 ml) and methanol (20 ml) was stirred at 50 to 65° C. for a period of about 8 to 10 h. The reaction mixture was evaporated under vacuum. To the residue water was added and the product was extracted in dichloromethane (100.0 ml). Benzoic acid (0.6 g) was added to the organic layer. The solvent was evaporated under reduced pressure and n-propanol was added to this residue and stirred at 25-30° C. The solid obtained was filtered & dried to give 1.35 gm of title compound.

Example 23

2-({6-[(3R)-3-aminopiperidin-1-yl]-3-methyl-2,4-dioxo-1,2,3,4-tetrahydropyrimidin-1-yl}methyl)benzonitrile benzoate A mixture of 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile (2.0) gm in mixture of ethanol amine (4 ml) and methanol (20 ml) was stirred at 50 to 65° C. for a period of about 8 to 10 h. The reaction mixture was evaporated under vacuum. To the residue water was added and the product was extracted in dichloromethane (100.0 ml). Benzoic acid (0.6 g) was added to the organic layer. The solvent was evaporated under reduced pressure. Propyl acetate was added to this residue and stirred at 25-30° C. The solid obtained was filtered & dried to give 1.35 gm of title compound.

Example 24

2-({6-[(3R)-3-aminopiperidin-1-yl]-3-methyl-2,4-dioxo-1,2,3,4-tetrahydropyrimidin-1-yl}methyl)benzonitrile benzoate A mixture of 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile (2.0) gm in mixture of ethanol amine (4 ml) and methanol (20 ml) was stirred at 50 to 65° C. for a period of about 8 to 10 h. The reaction mixture was evaporated under vacuum. To the residue, water was added and the product was extracted in dichloromethane (100.0 ml). Benzoic acid (0.6 g) was added to the organic layer. The solvent was evaporated under reduced pressure. Methyl acetate was added to this residue and stirred at 25-30° C. The solid obtained was filtered & dried to give 1.35 gm of title compound.

Example 25

2-({6-[(3R)-3-aminopiperidin-1-yl]-3-methyl-2,4-dioxo-1,2,3,4-tetrahydropyrimidin-1-yl}methyl)benzonitrile benzoate A mixture of 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile (2.0) gm in mixture of Hydrazine hydrate (4 ml) and methanol (20 ml) was stirred at 50 to 65° C. for a period of about 8 to 10 h. The reaction mixture was evaporated under vacuum. To the residue, water was added and the product was extracted in dichloromethane (100.0 ml). Benzoic acid (0.6 g) was added to the organic layer. The solvent was evaporated under reduced pressure and n-propanol was added to the residue and stirred for 25-30° C. The solid obtained was filtered & dried to give 1.2 gm of title compound.

Example 26

2-({6-[(3R)-3-aminopiperidin-1-yl]-3-methyl-2,4-dioxo-1,2,3,4-tetrahydropyrimidin-1-yl}methyl)benzonitrile benzoate A mixture of 2-({3-methyl-6-[(3R)-3-(5-methyl-1,3-dioxo-2,3-dihydro-1H-isoindol-2-yl)piperidin-1-yl]-2,4-dioxo-1,2,3,4-tetrahydropyrimidin-1-yl}methyl)benzonitrile (2.0) gm in mixture of methyl amine (6 ml) and methanol (20 ml) was stirred at 50 to 65° C. for a period of about 8 to 10 hr. The reaction mixture was evaporated under vacuum. To the residue, water was added and the product was extracted in dichloromethane (100.0 ml). Benzoic acid (0.6 g) was added to the organic layer. The solvent was evaporated under reduced pressure and n-propanol was added to the residue and stirred for 25-30° C. The solid obtained was filtered & dried to give 1.35 gm of title compound.

The invention claimed is:

1. A process for the preparation of alogliptin, a compound of formula I, or a salt thereof, comprising:

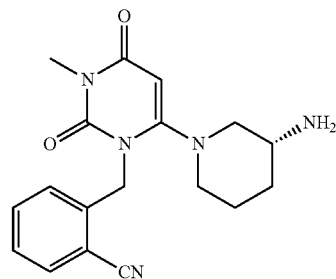

I a) methylating a compound of formula IV, to obtain a compound of formula V

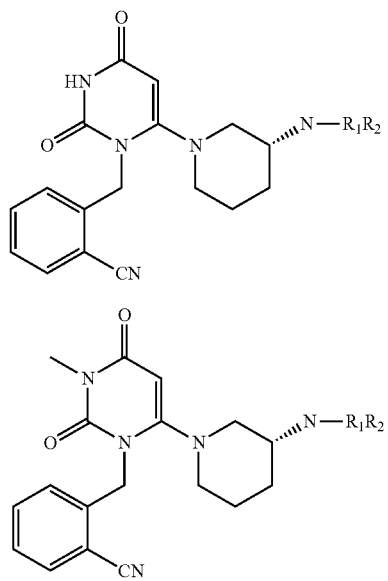

IV

V wherein $R_1$ and $R_2$ together with the nitrogen to which they are attached form a phthalimido group, wherein the aromatic ring of the phthalimido group is unsubstituted or substituted with one or more $R_3$ substituents selected from the group consisting of halogen, alkyl, nitro and amino; and b) deprotecting the compound of formula V to obtain compound of formula I.

2. The process of claim 1, wherein $R_1$ and $R_2$ together with the nitrogen to which they are attached form a phthalimido group and wherein $R_3$ on the aromatic ring of the phthalimido group is alkyl.

3. The process of claim 2, wherein the deprotection is carried out in presence of an amine.

4. A compound of formula IV having a purity of 90 to 95%:

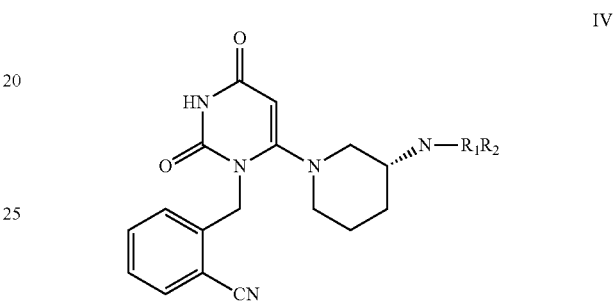

IV wherein $R_1$ and $R_2$ together with the nitrogen to which they are attached form a phthalimido group, wherein the aromatic ring of the phthalimido group is substituted with one or more $R_3$ substituents selected from the group consisting of halogen, alkyl, nitro and amino.

5. The compound of claim 4, wherein $R_1$ and $R_2$ together with the nitrogen to which they are attached form a phthalimido group and wherein $R_3$ on the aromatic ring of the phthalimido group is alkyl.

6. The compound of claim 5, wherein $R_1$ and $R_2$ together with the nitrogen to which they are attached form a phthalimido group and wherein $R_3$ on the aromatic ring of the phthalimido group is methyl, represented by compound of Formula Iva

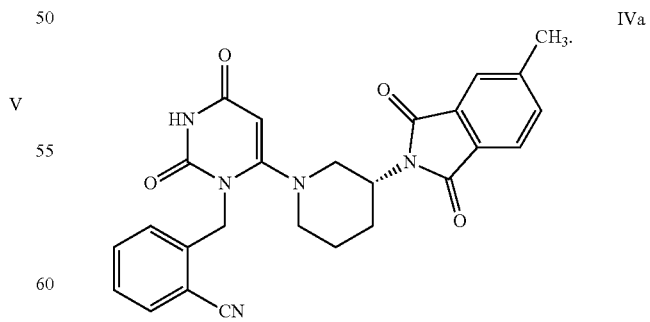

IVa

7. The process of claim 1, wherein the compound of formula IV is prepared by a process comprising
reacting a compound of formula II with a compound of formula III

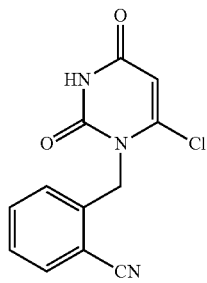

II

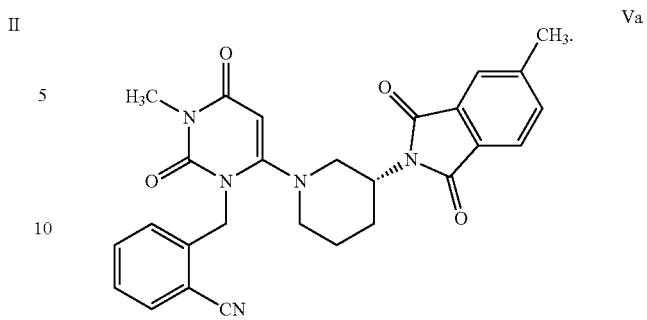

Va

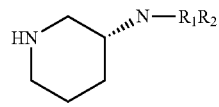

III wherein $R_1$ and $R_2$ together with the nitrogen to which they are attached form a phthalimido group, wherein the aromatic ring of the phthalimido group is unsubstituted or substituted with one or more $R_3$ substituents selected from the group consisting of halogen, alkyl, nitro and amino.

8. A compound of Formula Va having a purity more than 99%:

9. The process of claim 1, further comprising;
(a) treating alogliptin with an acid to form an acid addition salt of alogliptin; and
(b) treating the acid addition salt of alogliptin with a base followed by addition of benzoic acid to obtain alogliptin benzoate.

10. The process of claim 9, further comprising isolating alogliptin benzoate from a solvent selected from the group consisting of n-propanol, hexane, ethylene dichloride, methyl tertiary butyl ether, xylene, methyl tetrahydrofuran, propyl acetate, methyl acetate or mixtures thereof.

11. The process of claim 10, wherein the step of isolating comprises
a) subjecting alogliptin benzoate to slurrying in a solvent selected from the group consisting of n-propanol, hexane, ethylene dichloride, methyl tertiary butyl ether, xylene, methyl tetrahydrofuran, propyl acetate, methyl acetate or mixtures thereof to obtain solid alogliptin benzoate; and
b) filtering out the solid alogliptin benzoate, obtained in step a.

* * * * *